US011346777B2

(12) United States Patent
Mangold et al.

(10) Patent No.: US 11,346,777 B2
(45) Date of Patent: May 31, 2022

(54) VIBRATIONAL CIRCULAR DICHROISM SPECTROSCOPY

(71) Applicant: IRsweep AG, Stäfa (CH)

(72) Inventors: Markus Mangold, Stäfa (CH); Raphael Horvath, Stäfa (CH); Urszula Szczepaniak, Stäfa (CH)

(73) Assignee: IRsweep AG, Stäfa (CH)

( * ) Notice: Subject to any disclaimer, the term of this patent is extended or adjusted under 35 U.S.C. 154(b) by 0 days.

(21) Appl. No.: 17/171,205

(22) Filed: Feb. 9, 2021

(65) Prior Publication Data

US 2021/0247307 A1 Aug. 12, 2021

(30) Foreign Application Priority Data

Feb. 11, 2020 (GB) ..................................... 2001865

(51) Int. Cl.
*G01N 21/3581* (2014.01)
*G01N 21/19* (2006.01)
*G01N 33/483* (2006.01)

(52) U.S. Cl.
CPC ......... *G01N 21/3581* (2013.01); *G01N 21/19* (2013.01); *G01N 33/4833* (2013.01)

(58) Field of Classification Search
CPC .. G01J 3/453; G01J 3/0218; G01J 3/42; G01J 3/45; G01J 3/10; G01J 3/433;
(Continued)

(56) References Cited

U.S. PATENT DOCUMENTS

| 5,871,442 A | 2/1999 | Madarasz et al. |
| 10,753,801 B2 * | 8/2020 | Bourbeau Hébert ..... G01J 3/45 |

(Continued)

FOREIGN PATENT DOCUMENTS

| EP | 3441748 | 2/2019 |
| EP | 3865852 | 8/2021 |

(Continued)

OTHER PUBLICATIONS

Notification of Grant dated Jan. 25, 2022 in corresponding United Kingdom Application No. GB2001865.1.
(Continued)

*Primary Examiner* — Hoa Q Pham
(74) *Attorney, Agent, or Firm* — Renner, Otto, Boisselle & Sklar, LLP (57) ABSTRACT

A vibrational circular dichroism (VCD) spectroscopy method and apparatus that can significantly reduce the measurement time needed to acquire a differential absorption spectrum compared to known approaches. A dual-comb is generated by superimposing the outputs from two quantum cascade laser sources, thus providing a third comb interferogram with beat frequencies higher than the polarization modulation frequency. Consequently, for each of the left and right circularly polarized light, the measurement signal measures transmission through the sample across the full wavelength range of interest during each period of the polarization modulation. A complete vibrational spectrum is thus acquired in each modulation of a polarization modulator, instead of only acquiring data for a single wavelength during each modulation of the polarization, as in dispersive or tunable laser VCD, or only a single Fourier component of the spectrum, as in Fourier transform VCD.

18 Claims, 8 Drawing Sheets

(58) Field of Classification Search
CPC . G01S 17/88; G01B 9/02008; G01B 9/02007; G01N 21/3581; G01N 21/19; G01N 21/39; G01N 33/4833
USPC .......... 356/364–369, 451, 450, 454, 300–326
See application file for complete search history.

(56) References Cited

U.S. PATENT DOCUMENTS

| | | | |
|---|---|---|---|
| 2006/0001876 | A1 | 1/2006 | Gibbs et al. |
| 2007/0222988 | A1 | 9/2007 | Jiang et al. |
| 2011/0069309 | A1 | 3/2011 | Newbury et al. |
| 2011/0267625 | A1 | 11/2011 | Guelachvili et al. |
| 2012/0199742 | A1 | 8/2012 | Wagner et al. |
| 2014/0268148 | A1 | 9/2014 | Wang et al. |
| 2017/0201328 | A1 | 7/2017 | Hugi et al. |
| 2017/0307443 | A1* | 10/2017 | Bekal .................... G01J 3/2803 |
| 2018/0156718 | A1 | 6/2018 | Fleisher et al. |
| 2019/0128803 | A1 | 5/2019 | Ushida et al. |
| 2021/0063243 | A1* | 3/2021 | Anandarajah .......... G01N 21/45 |
| 2021/0063306 | A1* | 3/2021 | Gianella ................... G01J 3/45 |

FOREIGN PATENT DOCUMENTS

| | | |
|---|---|---|
| JP | 2017138129 | 8/2017 |
| KR | 2010/0091280 A | 8/2010 |
| WO | 01/63231 | 8/2001 |
| WO | 2007/109344 | 9/2007 |
| WO | 2015/193282 | 12/2015 |
| WO | 2018/115446 A1 | 6/2018 |

OTHER PUBLICATIONS

Examination Report and Notification of Intention to Grant under Section 18(4) dated Nov. 24, 2021 in corresponding United Kingdom Application No. GB2001865.1.

Keiderling, T.A. Instrumentation for Vibrational Circular Dichroism Spectroscopy: Method Comparison and Newer Developments. Molecules 2018, 23, 2404

Keiderling, T.A. Vibrational Circular Dichroism. Appl. Spectrosc. Rev. 1981, 17, 189-226.

Long, F.; Freedman, T.B.; Hapanowicz, R.; Nafie, L.A. Comparison of step-scan and rapid-scan approaches to the measurement of mid-infrared Fourier transform vibrational circular dichroism. Appl. Spectrosc. 1997, 51, 504-507.

Rüther, A.; Pfeifer, M.; Lórenz-Fonfría, V.A.; Lüdeke, S. pH Titration Monitored by Quantum Cascade Laser-Based Vibrational Circular Dichroism. J. Phys. Chem. B 2014, 118, 3941-3949 doi.org/10.1021/jp4122886.

Lüdeke, S; Pfeifer, M; and Fischer, P Quantum-Cascade Laser-Based Vibrational Circular Dichroism doi.org/10.1021/ja200539d, J. Am. Chem. Soc. 2011, 133, 5704-5707.

Pfeifer, M; Lüdeke, S; and Fischer, P Mid-IR laser-based vibrational optical activity, Proc. SPIE 8219, Biomedical Vibrational Spectroscopy V: Advances in Research and Industry, 821906 (Feb. 1, 2012); doi: 10.1117/12.906421.

* cited by examiner

VIBRATIONAL CIRCULAR DICHROISM SPECTROSCOPY

RELATED APPLICATIONS

This application claims priority to GB Application No. 2001865.1 filed on Feb. 11, 2020, the entire disclosure of which is hereby incorporated by reference.

BACKGROUND OF THE INVENTION

The invention relates to circular dichroism (CD) spectroscopy in the infrared (IR). CD spectroscopy in the IR region is referred to as vibrational CD (VCD). VCD is a widely used standard method for determination of absolute stereochemistry. VCD is also used for biomolecule characterization and for following dynamic processes. Initial VCD instruments were constructed in the same manner as conventional ultraviolet-to-visible (UV-vis) circular dichroism (CD) spectrometers, but with various components altered to provide functionality in the infrared (IR). Typical CD instruments have bright broadband sources and dispersive optics that utilized a sequentially scanned prism or grating to select the wavelength bandpass that passed through a slit. To operate in the IR and maximize signal-to-noise ratio (S/N), many alterations to conventional CD designs were needed. Most VCD spectrometers use grid polarizers, holographically formed on IR transmitting, isotropic substrates. The monochromator output is passed through a wire-grid polarizer and a photo-elastic modulator (PEM) to induce a fast polarization modulation, where fast means in the tens of kHz range. Semiconductor detectors are used to provide the sensitivity needed to detect very low amplitude modulations, and to give the speed of response necessitated by the high modulation frequencies. The detector signal is then demodulated at the PEM frequency to retrieve the VCD signal [1, 2].

The pioneering work of Nafie and co-workers in the development of Fourier transform (FT) VCD instrumentation shifted the methodology, and such instruments now dominate the VCD field. They commonly utilize a commercial FTIR to which polarization optics as well as processing electronics and software are added for purposes of VCD measurement. The interferometer used is typically of rapid-scan design, incorporating a KBr beam splitter coated for mid-IR use and a glow bar or other heated ceramic source. Its output beam is directed through a polarizer (wire grid) and PEM (ZnSe) and onto a sample, after which it is focused onto a Mercury Cadmium Telluride (MCT) detector, typically with a ZnSe lens [1, 3].

More recently, Lüdeke and co-workers have developed a quantum cascade laser (QCL) VCD system which replaces the broadband IR source, e.g. glow bar, and monochromator of previous systems with a tunable laser source in the form of a QCL. Their results demonstrated that a QCL source can be used to measure VCD and replicate FT-VCD results [1, 4].

Notwithstanding these significant advances in VCD, the main issue preventing the more widespread use of VCD is the long measurement time required for obtaining good signal-to-noise ratio (SNR) VCD data. Typically, VCD signals of fundamental transitions are ten thousand to one hundred thousand times lower than normal absorption signals. Since, for avoidance of non-linearity issues, the normal absorption must be kept below one optical density (OD), the signals to be detected are generally on the order of 10-100 micro optical density (µOD). To obtain a signal to noise ratio of at least SNR=10, measurement times of several hours are common.

SUMMARY OF THE INVENTION

According to a first aspect of the invention there is provided a method of acquiring a circular dichroism spectrum measuring differential absorption of left and right circularly polarized light by a sample over a wavelength range of interest, the method comprising:

arranging a sample in a sampling beam path;

arranging a polarization modulator in the sampling beam path before the sample, the polarization modulator being switchable between two states to output left and right circularly polarized light respectively;

combining first and second light signals containing respective first and second frequency combs into the sampling beam path, the first and second frequency combs consisting of respective finite series of discrete frequencies separated by first and second spacings defined as first and second free spectral ranges respectively;

arranging a sample detector operable to output a measurement signal in the sampling beam path after the sample, the sample detector having a detection bandwidth that covers a frequency range corresponding to beat frequencies of a third frequency comb that is detected by the sample detector as the measurement signal as a result of heterodyne mixing of the first and second light signals;

periodically switching the polarization modulator between its two states at a polarization modulation frequency to output left and right circularly polarized light respectively; and setting the frequencies of the first and second light signals such that the beat frequencies of the third frequency comb are higher than the polarization modulation frequency so that for each of the left and right circularly polarized light the sample detector's measurement signal measures transmission through the sample across the wavelength range of interest during each period of the polarization modulation.

Embodiments of the disclosure can thus provide a VCD spectroscopy method and corresponding spectrometer that significantly reduce the measurement time needed to acquire a differential absorption spectrum with good signal-to-noise ratio compared to known VCD methods and apparatus. In our approach, we acquire a full vibrational spectrum within each polarization modulation, instead of only acquiring data for a single wavelength during each modulation of the polarization (as in dispersive or tunable laser VCD) or a single Fourier component of the spectrum (as in FT VCD). Our experimental results with a pair of complimentary test samples show that a VCD spectrum with good signal-to-noise ratio can be acquired in as little as two seconds of measurement time.

In some embodiments, the third frequency comb's beat frequencies, i.e. beat notes, are synchronized with the periodic switching of the polarization modulator, e.g. using a suitable controller, such that each of the beat frequencies is an integer multiple of the polarization modulation frequency, e.g. 2, 3, 4, 5, etc., or 52, 53, 54, 55 etc. or any higher harmonics, e.g. 25, 28, 31, 34, etc. (i.e. increments of more than one).

In other embodiments, the third frequency comb's beat frequencies, i.e. beat notes, are between 1-2 and 4-5 orders of magnitude higher than the polarization modulation frequency. While in most implementations, there will be an orders of magnitude difference in the respective frequencies, the ratio of frequencies could be as low as two, i.e. the beat frequencies of the third frequency comb should be at least twice the polarization modulation frequency; assuming that all beat frequencies are retained in the determination of the differential absorption spectrum. If the lowest beat frequencies were discarded from the collected signal data, then the ratio could be less than two.

According to a second aspect of the invention there is provided a QCL dual comb circular dichroism spectrometer operable to measure a sample's differential absorption of left and right circularly polarized light over a wavelength range of interest. The spectrometer comprises:

- a polarization modulator that is periodically switchable between two states at a polarization modulation frequency to output left and right circularly polarized light respectively;
- a sample holder configured to receive a sample to be measured in a sample space so that a sample held in the sample holder receives light output from the polarization modulator;
- a first semiconductor laser source, serving as a local oscillator, operable to output a first light signal containing a first frequency comb consisting of a finite series of discrete frequencies separated by a first spacing defined as a first free spectral range;
- a second semiconductor laser source, serving as an interrogator, operable to output a second light signal containing a second frequency comb consisting of a finite series of discrete frequencies separated by a second spacing defined as a second free spectral range;
- a beam combiner configured to receive and superimpose the first and second light signals to form a combined light signal and to direct the combined light signal to be input into the polarization modulator;
- a sample detector operable to output a measurement signal and arranged to receive the combined light signal after it has traversed the sample space, the sample detector having a detection bandwidth that covers a frequency range corresponding to beat frequencies of a third frequency comb that is detected by the sample detector as the measurement signal as a result of heterodyne mixing of the first and second light signals;
- a controller configured to output first and second control signals to the first and second semiconductor laser sources to set the frequencies of the first and second light signals such that the resultant beat frequencies of the third frequency comb are higher than the polarization modulation frequency so that for each of the left and right circularly polarized light the sample detector's measurement signal measures transmission through the sample across the wavelength range of interest during each period of the polarization modulation; and
- a data acquisition module arranged to collect data from the measurement signal and configured to determine a differential absorption spectrum for a sample over the wavelength range of interest from the collected data.

In some embodiments, the spectrometer further comprises a frequency demodulator arranged to extract an error signal from the measurement signal, the error signal being fed back to the controller, the controller being configured to determine a correction signal from the error signal in a control loop to at least one of the first and second semiconductor laser sources derived from the error signal so as to lock the first laser source to the second semiconductor laser source in a master-slave configuration.

In other embodiments, the spectrometer further comprises a first RF generator operable to generate a first reference signal at a first RF frequency that is matched to the first free spectral range, the first RF generator being connected to inject the first reference signal into the cavity of the first semiconductor laser source to lock the first free spectral range to the first RF frequency and optionally also a second RF generator operable to generate a second reference signal at a second RF frequency that is matched to the second free spectral range, the second RF generator being connected to inject the second reference signal into the cavity of the second semiconductor laser source to lock the second free spectral range to the second RF frequency.

The semiconductor laser sources may be quantum cascade lasers (QCLs) based on transitions between subbands, or interband cascade lasers (ICLs) based on transitions between bands.

In our implementation, the polarization modulator comprises a linear polarizer arranged in series in the sampling beam path with a photo-elastic modulator (PEM). The photo-elastic modulator having a resonance frequency that defines the polarization modulation frequency. A PEM is made of a section of a material that is optically transparent over its operating wavelength range and which exhibits strain-induced birefringence when resonated at its resonance frequency. Suitable materials for infrared operating wavelengths suitable for VCD are calcium fluoride, silicon and zinc selenide, for example. The bar is dimensioned to provide a resonance frequency of a desired magnitude. The PEM also includes a transducer, typically a piezoelectric transducer, which is mechanically connected to the bar of birefringent material and can be driven at the bar's resonance frequency in order to resonate the bar. A PEM is thus only operable at its resonance frequency. Commercially available PEMs that are suitable for use in embodiments of the disclosure typically have resonance frequencies between 20 kHz to 100 kHz, such as the 37 kHz ZnSe PEM we have used in our experiments that are discussed further below.

In practical implementations some kind of data acquisition module will be used to collect data from the measurement signal, wherein the data contained in the measurement signal in each period of the polarization modulation is sufficient to determine a differential absorption spectrum over the wavelength range of interest. The data acquisition module may additionally include a processor operable to determine the differential absorption spectrum from the collected data. The data acquisition module may serve to aggregate the differential absorption spectra that are obtained from the measurement signal in each polarization modulation period. As the data accumulates, the SNR will improve.

In addition to a sample detector, it is useful to also have a normalizing detector. The normalizing detector, like the sample detector, has a detection bandwidth covering the third frequency comb. The normalizing detector is arranged to receive a combined light signal from superimposing the first and second light signals, neither of which has traversed the sample. The signal from the normalizing detector can be used to normalize the signal from the sample detector, e.g. by dividing the amplitudes of the beat notes measured in the sample detector signal by the amplitudes of the beat notes measured in the normalizing detector signal. The data acquisition module is arranged also to collect the signal from the normalizing detector, which we refer to as a normalizing signal. The normalizing signal can then be compared with the simultaneously obtained measurement signal.

In some embodiments, the first and second laser sources are free running. By free running we mean that the lasers are allowed to lase optically independently of each other, rather than being locked together, e.g. by phase locking. In other embodiments, the first and second laser sources may be locked, e.g. in a master-slave relationship.

In some embodiments, the first and second control signals are voltage signals that are input to first and second current drivers, which translate the first and second control signals into a desired setting of the first and second drive currents applied to the first and second laser sources, thereby to fix the first and second frequency combs at desired positions in frequency space. This will likely be the most common implementation, but there are other ways to transfer the control signals onto the laser sources. Instead or as well as the above, the first and second control signals, or first and second components thereof, may be applied to adjust the temperature of the first and second laser sources via first and second heaters arranged in thermal communication with the first and second laser sources. Other possibilities may also be available based on any parameter that can be varied so as to set refractive index or temperature of the sources, e.g. broadband illumination of a part of the source.

BRIEF DESCRIPTION OF THE DRAWINGS

This invention will now be further described, by way of example only, with reference to the accompanying drawings.

DETAILED DESCRIPTION

Definitions

Frequency comb: a form of laser output consisting of a series of discrete, equally spaced frequencies, referred to as teeth.

Free spectral range (FSR): the spacing in optical frequency between two neighboring comb teeth. In a dual-comb spectrometer, the respective FSRs of the local oscillator and interrogator will be almost the same, i.e. only marginally different, perhaps differing only by 1/5000. Hence, in dual-comb spectroscopy (DCS) we usually refer to "the" FSR even though there are two marginally different FSRs.

Beat frequencies/notes: a term used to describe the heterodyne frequencies generated by beating of the local oscillator and interrogation beams in an optical heterodyne system as a consequence of the difference in their FSRs.

Spectral sampling period: spectral distance between adjacent measurement points, sometimes referred to as point spacing.

Spectral resolution: minimum resolvable spectral distance in frequency or wavelength between two spectral lines.

DESCRIPTION OF FIGURES

Figure 1:
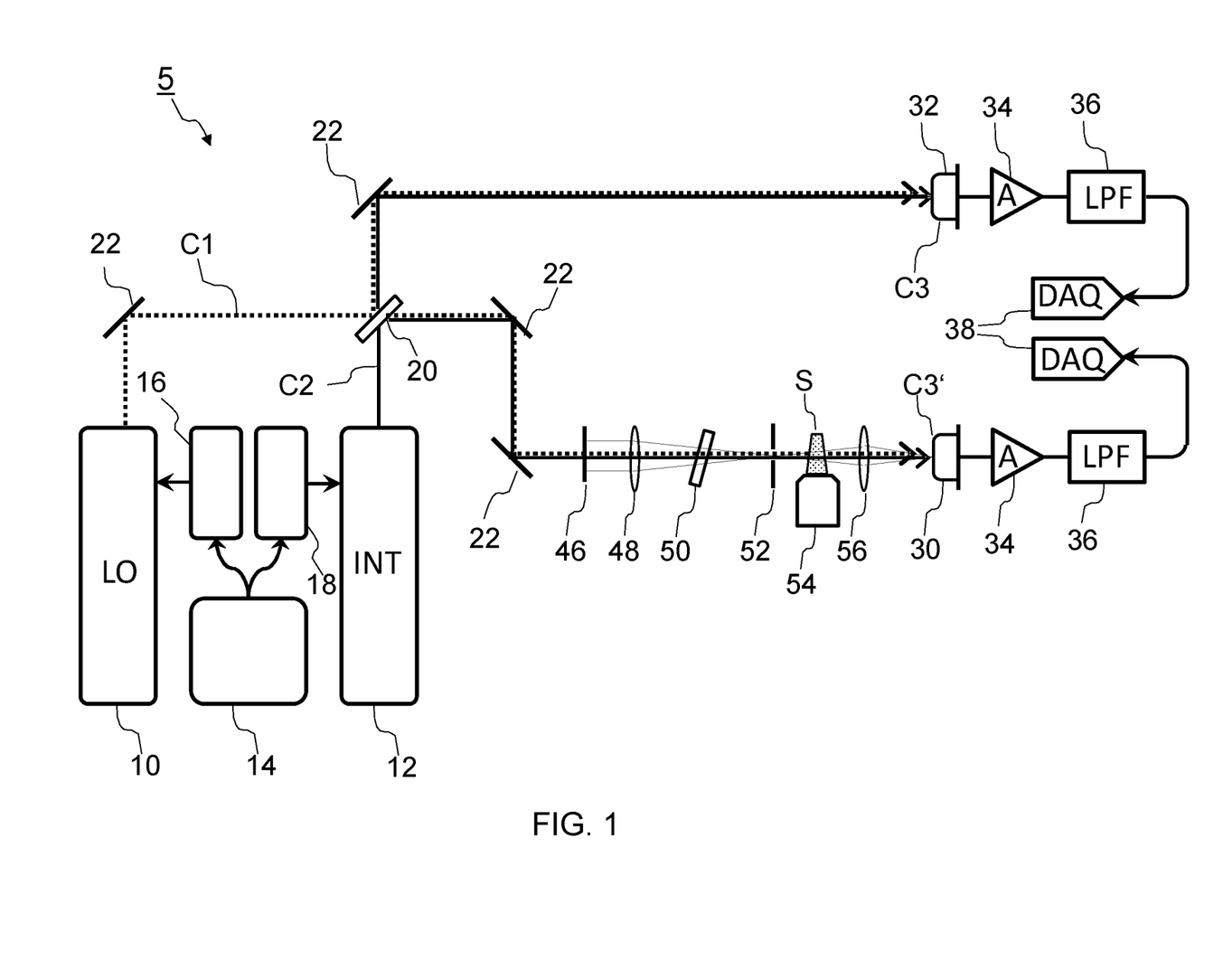
FIG. 1 is a schematic drawing of a VCD spectrometer according to an embodiment of the disclosure.

FIG. 1 is a schematic drawing of a VCD spectrometer 5 according to an embodiment of the disclosure. This spectrometer configuration is one in which both the interrogating and local oscillator comb beams are transmitted through the sample, so that the amplitude response of the sample, i.e. its absorption, is measured. The VCD spectrometer 5 is based around a pair of laser sources, namely a QCL 10 serving as a local oscillator and a QCL 12 serving as the interrogator. The first and second laser sources 10, 12 are free running in the example configuration shown. By free running we mean that the lasers are allowed to lase optically independently of each other, rather than being locked, e.g. by phase locking. The two QCLs 10, 12 generate respective light signals containing respective frequency combs C1 and C2, each having frequencies consisting of a finite series of discrete frequencies. Each of combs C1 and C2 may for example contain on the order of 100 phase-locked optical modes in a typical implementation. Combining the first and second light beams results in the photocurrent output by a photodetector receiving such a combined beam generating a superposition of sinusoidal oscillations in the photocurrent, with a set of frequencies evenly spaced by the difference between the first and second spacings, representing a third frequency comb which is shifted several orders of magnitude to lower frequencies relative to the first and second frequency combs. We refer to the frequency range of the third comb as lying in the RF, following normal usage, although the frequency range may not in all cases be in the radio frequency range (i.e. 20 kHz-300 GHz) as would be understood by an RF engineer.

The QCLs 10, 12 are driven by respective current drivers 16, 18 for supplying suitable drive currents to the QCLs. The laser drive currents may beneficially be low-pass filtered (e.g. cut-off below 100 Hz) although low-pass filtering is not necessary in all cases. For example, in our prototype system, each laser emits around 300-400 mW of average power at 1.1 A (typical drive current). The current drivers 16, 18 are in turn controlled by respective voltage control signals supplied by a driver controller 14 which sets the levels for the voltage control signals. The voltages output by the driver controller 14 are then applied to generate corresponding drive currents to drive the QCLs 10 and 12 so that the QCLs' combined beams sample over a desired RF range.

The output beams from QCLs 10 & 12 are split, guided and recombined by suitably arranged beam splitter(s) 20 and plane mirrors 22, for example as illustrated. The beam splitting will aim to be 50/50 in typical implementations, i.e. will aim to split the beam power approximately equally into two. Both the local oscillator comb C1 and the interrogating frequency comb C2 traverse the sample S which attenuates their amplitude through absorption and also induces a phase shift. The sample S occupies a sample space.

The sample S is arranged in an optical subassembly for VCD comprising in order of traversal by the sampling beams C1 and C2: a linear polarizer 46; a focusing lens 48; a PEM 50 having a fast axis and a slow axis; an aperture 52 such as an adjustable iris providing an approximately circular aperture of adjustable diameter; a sample cell holder 54 in which a sample cell S may be removably mounted; and a further focusing lens 56 for focusing the beams that have passed through the sample cell S onto the detector 30. The focusing lens 48 serves to reduce the beam diameter incident on the PEM 50 and to focus the beam onto the aperture 52 as schematically illustrated. The PEM 50 dynamically changes its birefringence and so periodically modulates the polarization of the incoming light. The PEM 50 used in our experiments is based on a ZnSe bar and has a modulation frequency of 37 kHz and an operating wavelength range for use as a quarter-wave plate of 2-18 µm. The modulation amplitude is adjustable and was set in our measurements to be $\pm\lambda/4$ for the central emission wavelength of the frequency combs output from our QCL sources 10, 12. For the linear polarizer 46 arranged before the PEM 50 (as considered in the beam direction) we used a wire-grid polarizer. The linear polarizer 46 is aligned with its polarization axis set at 45 degrees to the fast axis of the PEM 50. In our set-up, the PEM has a polarization modulation frequency of 37 kHz to provide switching at time intervals of $1/37$ milliseconds corresponding to every 27 microseconds. With this arrangement, the polarization of the light beams is modulated alternately to output right-hand circularly polarized light from a linearly polarized input and to output left-hand circularly polarized light from a linearly polarized input. In every modulation period, the beam polarization gradually changes from right handedly polarized to left handedly polarized and back to right handedly polarized following a sine wave modulation. The sample cell holder 54 and optionally also the other components of the VCD subassembly 46, 48, 50, 52 and 56 may be mounted on translation stages, such as xyz-stages or xy-stages to allow for positional adjustment. The aperture's limited size in combination with the tilt of the PEM serve to suppress internal reflections from the PEM surfaces.

The lens 48 in our set-up has a focal length of 200 mm. The purpose of the lens 48 is to ensure that the beam incident on the PEM 50 has a small diameter (e.g. <1 mm). The PEM 50 is tilted somewhat to the optical axis of the beams C1 and C2. This slightly tilted arrangement of the PEM 50 in relation to orthogonal to the optical (beam) axis ensures that light which is reflected on both inner surfaces of the PEM 50 are offset from the optical axis by an amount larger than the aperture diameter (e.g. >1 mm), so that the aperture 52 blocks these reflected beams and so removes them from the signal incident on the detector 30. Interference fringes caused by internal reflection in the PEM 50 are thus suppressed. The lens 56 focuses the signal onto the detector 30. The lens 56 in our set-up has a focal length of 25 mm.

Components of the local oscillator frequency comb C1 and the interrogating frequency comb C2 traverse the sample S which attenuates their amplitudes through absorption and also shifts their phases. Since components of both comb signals C1 and C2 traverse the sample, the phase shifts are the same, so the interferogram C3' of the combined signal of combs C1 and C2 measured by the detector 30 carries only amplitude modulation information from the sample and no phase information. The photodetector 30 is referred to as the sample detector. The detector 32, referred to as the normalizing detector, measures the reference combined comb C3 which is an interferogram of the other components of the combs C1 and C2 from the beamsplitter that have not traversed the sample S. The signal C3 taken by the normalizing detector 32 provides a basis for normalizing the measurement signal C3' taken by the sample detector 30.

It will be appreciated that equivalent optical fibre components could be used instead for manipulating the beams through the sample and onto both the sample detector 30 and normalizing detector 32.

The signals picked up by the photodetectors 30, 32 are amplified by respective amplifiers 34 which are serially connected to respective low-pass filters (LPFs) 36 which serve to exclude frequencies from outside the range of the third frequency comb C3. The filtered signals are then supplied to the inputs of respective data acquisition (DAQ) modules 38 with analogue to digital converters (ADCs) which digitize the signals and supply them to the inputs of digital electronics provided for data acquisition and logging, e.g. in a computer that may also be used for controlling the driver controller 14 and any other components that either require control inputs or provide sensor signals relevant for the QCLs, e.g. to keep the QCLs at a stable temperature. For example, the QCL lasers 10, 12 may be housed in respective water-cooled enclosures with a thermoelectric element in each housing to set and maintain the laser temperature at 25° C. In one example, the LPFs 36 have a pass-band of 50-1050 MHz. In one example, the ADCs are 14-bit and operated with a sampling rate of 2 Gsamples/s. The QCL output powers are chosen so that the power reaching the photodetectors 30, 32 is within the linear response range of the photodetectors 30, 32. The signal collected by the normalizing photodetector 32 serves to cancel or suppress common mode fluctuations between the free running QCLs due to power and frequency fluctuations.

Figure 2:
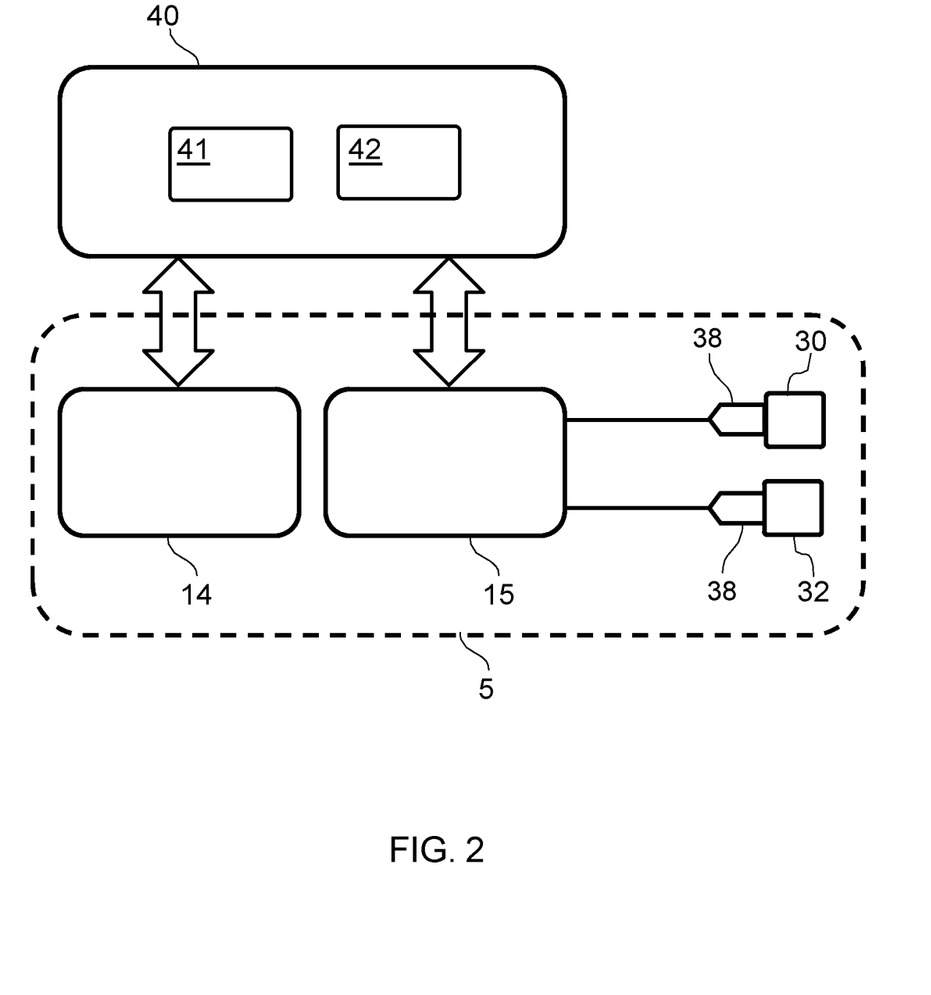
FIG. 2 shows the VCD spectrometer of FIG. 1 in combination with a computer for control and data acquisition.

FIG. 2 shows in functional blocks the spectrometer 5 of FIG. 1 in combination with a computer 40 to provide a controller for control of the spectrometer 5, including the driver controller 14, and to provide a data acquisition module for data acquisition and optionally also data processing function for assembling VCD spectra from the acquired data. The computer 40 is able to program and actuate the driver controller 14 via a suitable interface which may be a bus interface. The computer 40 is also connected to receive and store the digitized data derived from the photodetectors 30, 32 and DAQs 38 via a data acquisition module 15. The computer 40 comprises and/or has access to suitable storage 42 for the data. The laser driver controller 14 and/or the data acquisition module 15 could be integrated into the computer 40. After each measurement, or batch of measurements, the raw digitized data may be written to disk, or otherwise stored in memory, without any initial processing. In one example, there is ca. 1 GByte of data per measurement scan. The computer 40 further includes a processor or processing unit 41, which may include a graphics processor unit (GPU) or field programmable gate array (FPGA) or a programmable logic array (PLA) for real-time data processing.

In summary, the embodiment discloses a VCD spectrometer 5 operable to measure a sample's differential absorption of left and right circularly polarized light over a wavelength range of interest. Principal components of the spectrometer are: a PEM 50, a sample holder 54; first and second QCL sources 10, 12 acting as local oscillator and interrogator respectively; beam splitting/combining and routing optical components 20, 22; and detectors 30, 32 for receiving measurement and normalizing beams that have and have not traversed the sample respectively. For spectrometer control, signal collection and data processing suitable computing components are provided, namely a personal computer 40 with connected laser driver controller 14 for controlling the QCLs 10, 12 and a data acquisition module 15 arranged to collect data from the DAQs 38 which digitize the outputs from the detectors 30, 32.

An optional refinement to what has been described above is to lock the output of one or both of the lasers 10 and 12 by measuring the RF frequency modulation in the mixed signal detected by detector 30 and/or 32 and then feeding this back as an error signal which is used as a basis for adjusting the drive current of one or both of the lasers 10 and 12. The drive current adjustment could be done directly by adding a small correcting adjustment current to the drive current output by the driver controller 14 (fast loop). Alternatively, the drive current adjustment could be done indirectly by inputting the error signal to the driver controller 14, the error signal then being used by the driver controller 14 to stabilize the voltage it is applying to generate the drive current (slow loop). The error signal may be generated from the RF signal(s) using a frequency demodulator, such as a phase detector, phase comparator or low pass filter. In addition a lock-in amplifier (analogue or digital) may be used in combination with a frequency demodulator to generate the error signal. The error signal can be based on a measurement of the drift of one or more of, or potentially all of, the frequencies of either one of, or both of, the combs C3 and C3'. The same FPGA and/or GPU as mentioned above can be used to determine an appropriate drive current correction signal from the error signal. A master-slave configuration is thus provided between the interrogating comb laser source 12 and the local oscillator comb laser source 10.

Figure 3:
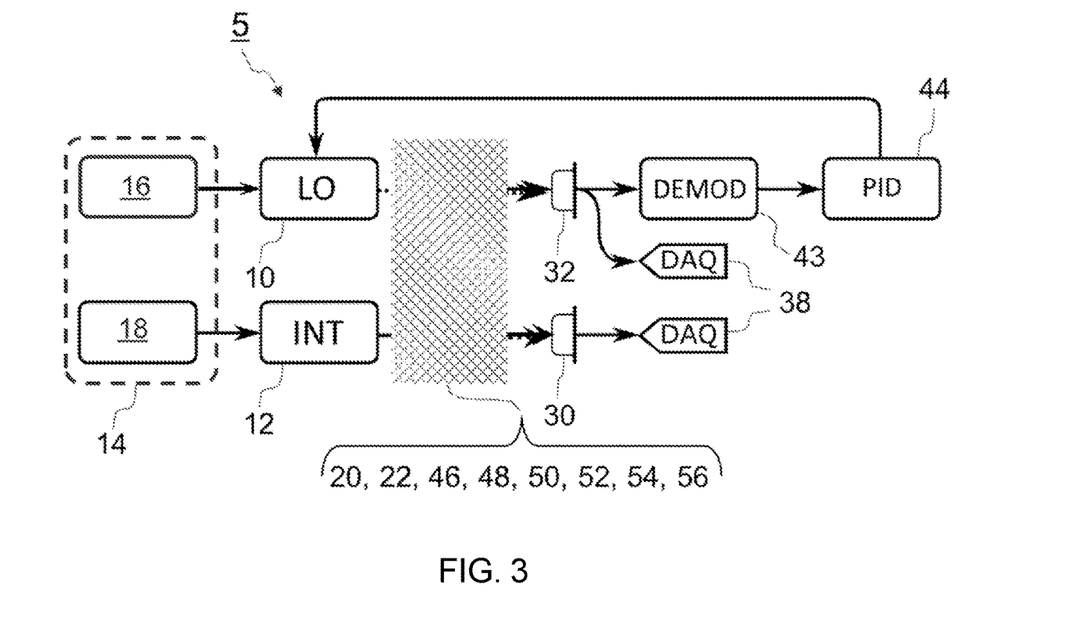
FIG. 3 shows an example fast feedback loop architecture to modify the configuration of FIG. 1 so as to lock the laser outputs in a master-slave configuration.
Figure 4:
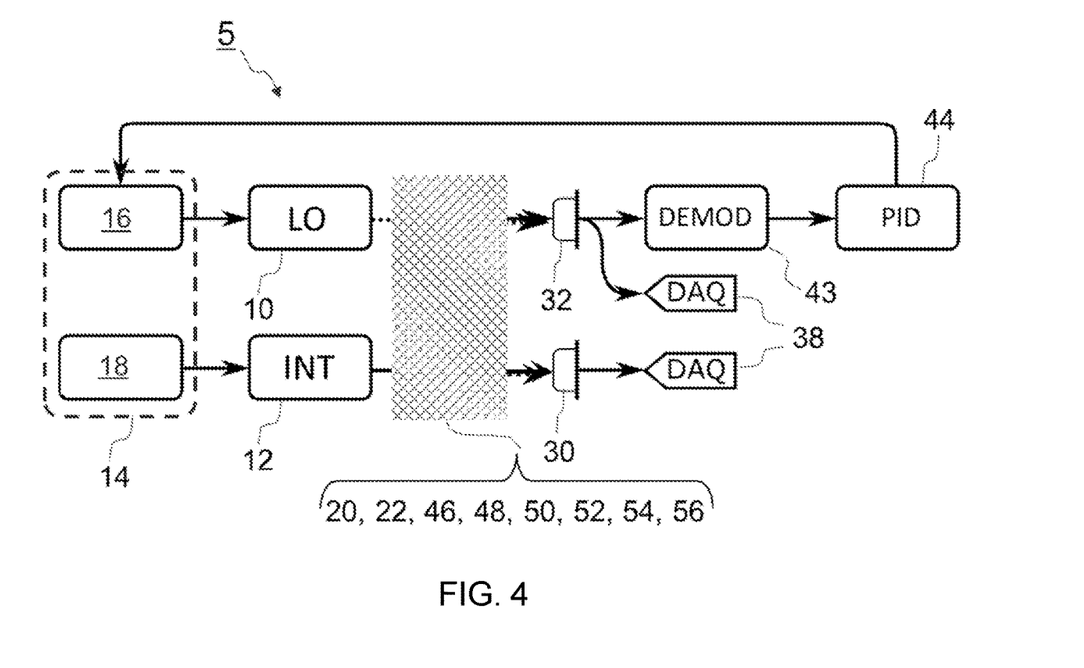
FIG. 4 shows an example slow feedback loop architecture to modify the configuration of FIG. 1 so as to lock the laser outputs in a master-slave configuration.

FIGS. 3 and 4 illustrate respective spectrometers 5 embodying the disclosure which have example fast loop and slow loop feedback architectures in which the output of the first laser source 10 is locked based on an error signal derived from the signal received at detector 32, thereby providing the above-described master-slave configuration. The illustrations omit some of the detail from FIG. 1 when this is not directly relevant for the feedback loop, e.g. the drivers 16, 18, the amplifiers 34 and the filters 36 are omitted from the illustrations. In both examples, the RF signal from the comb C3 measured by detector 32 is used as input to a frequency demodulator 43, and the error signal output from the frequency demodulator 43 is supplied to a proportional-integral-differential (PID) controller 44 which generates a correction signal that is used to stabilize the drive current for the first laser source 10. It is also noted that the feedback schemes shown in FIGS. 3 and 4 could be implemented with any desired sample setup, e.g. as shown in FIG. 1 or any other suitable arrangement. The fact that these feedback loop architectures are generic to the optical routing from the lasers to the detectors via the sample is indicated schematically with the cross-hatched box in both FIG. 3 and FIG. 4.

FIG. 3 shows a fast loop implementation using a PID controller 44 to generate a correction signal that is fed back to adjust the laser drive current. The signal C3 and/or C3' of either detector 30, 32 in the reference setup is frequency demodulated by a frequency demodulator 43 to generate an error signal. The frequency demodulation can be performed before or after DAQ 38, i.e. on the analogue signal or the digitized signal. The former option is illustrated. The frequency demodulated signal generated by a frequency demodulator 43 is fed into a PID controller 44 to generate a correction signal. The correction signal is used to alter the laser drive current (or any other drive parameter used to adjust the frequency output of the device, such as temperature) of the laser source 10. The drive current can be adjusted directly on the laser driver, e.g through an analogue input on a QCL 2000 Wavelength Electronic driver. Another method would be to employ a field effect transistor (FET) after the laser current output to alter the drive current at a fast rate.

FIG. 4 shows a slow loop implementation using a PID controller 44 to generate a correction signal that is fed back to the driver controller 14 to stabilize its output and hence, through the adjusted waveform, keep the laser drive current constant at the set value. The signal C3 and/or C3' of either detector 30, 32 in the reference setup is frequency demodulated by a frequency demodulator 43 to generate an error signal. The frequency demodulation can be performed on the analogue signal or the digitized signal. The former option is illustrated. The PID controller 44 determines a correction signal from the error signal, which is then output by the PID controller 44 and supplied as an input to the driver controller 14, the magnitude of the correction signal then being used to make fine adjustments to the voltage that the driver controller 14 is generating for the first laser source 10. The corresponding voltage generated by the driver controller 14 for the second laser source 12 need not be included in the feedback loop (as illustrated). It will be understood that the PID controller 44 can be integrated in a computer platform and be part of the control computer & data logger 40.

In respect of both slow and fast feedback loops, since both detectors will generally be the same, they will have the same bandwidth specifications, so operating the feedback loop based on signal from only one of the detectors will in many cases be adequate to keep the signal within the bandwidth of both detectors.

The above discussion on tuning the QCLs to acquire data was made in relation to adjusting the laser drive currents. It will be understood that the lasers may also be adjusted by adjusting their temperatures, and temperature adjustment may be used instead of current adjustment, or the lasers may be controlled by a combination of drive current and temperature adjustment. Other adjustment possibilities may also be available based on any parameter that can be varied so as to modulate refractive index or temperature of the sources, e.g. broadband illumination of a part of the source or RF-injection as is now discussed.

Further details of how to acquire data in a dual-comb setup may be found in WO 2015/193282 A1 [5], the full contents of which is hereby incorporated by reference.

Figure 5:
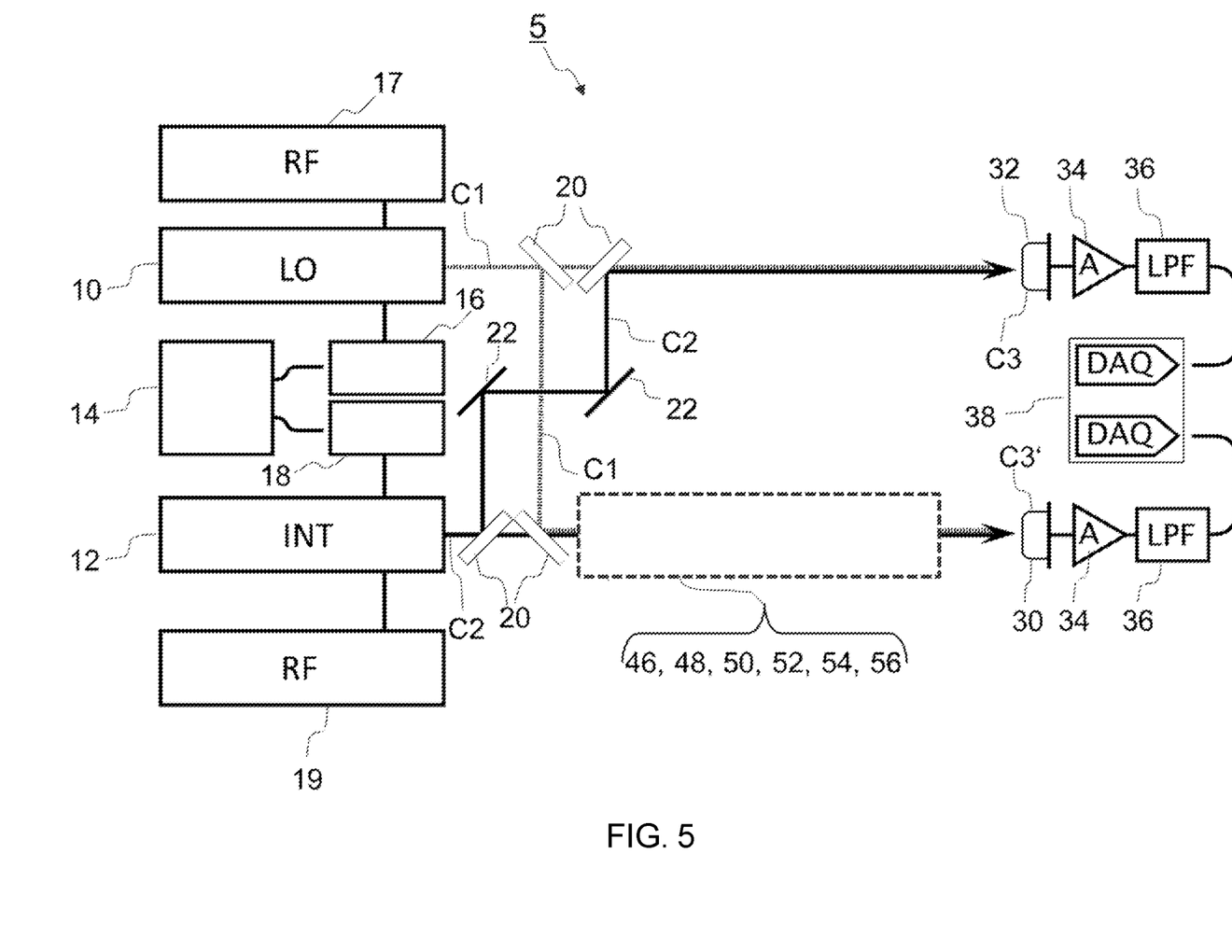
FIG. 5 is a schematic drawing of a VCD spectrometer according to another embodiment with RF-injection locking of the lasers.

FIG. 5 is a schematic view of another embodiment which has the same type of sample configuration as FIG. 1 in that both the interrogating and local oscillator comb beams C1, C2 are transmitted through the sample. In this embodiment there are, compared with FIG. 1, RF-generators 17 and 19 provided to supply RF-injection currents to the respective laser sources 10 and 12. It is an inherent property of a semiconductor QCL (and also an interband cascade laser) that the FSR changes upon changes of drive current, temperature, or other environmental parameters which will cause a corresponding change in the frequency spacing of the resultant RF frequency comb C3. To avoid these effects, the FSRs of the frequency combs C1 and C2 generated by the laser sources 10 and 12 can be locked to a particular reference RF frequency by applying an RF signal with a frequency that is equal to, or near equal to, the FSR (i.e. round-trip frequency) of the laser source. The laser's FSR will then lock to the reference RF frequency provided that the reference RF frequency is within the locking range of the laser. The reference frequency is therefore ~1 FSR (or any harmonic of said frequency). A suitable RF-generator for this task is any general purpose RF generator that can operate at the frequencies of the FSRs which it is desired to lock, such as a Rhode & Schwartz SMF 100A. The reference RF signal is preferably injected into both ends of the laser cavity with appropriate phase for enhanced RF-injection, but in some embodiments could be injected into only one end of the laser cavity. It is also noted that FIG. 5 shows a different routing and splitting of the QCL output beams compared to FIG. 1 using multiple beam splitters 20 as well as multiple mirrors 22.

Figure 6:
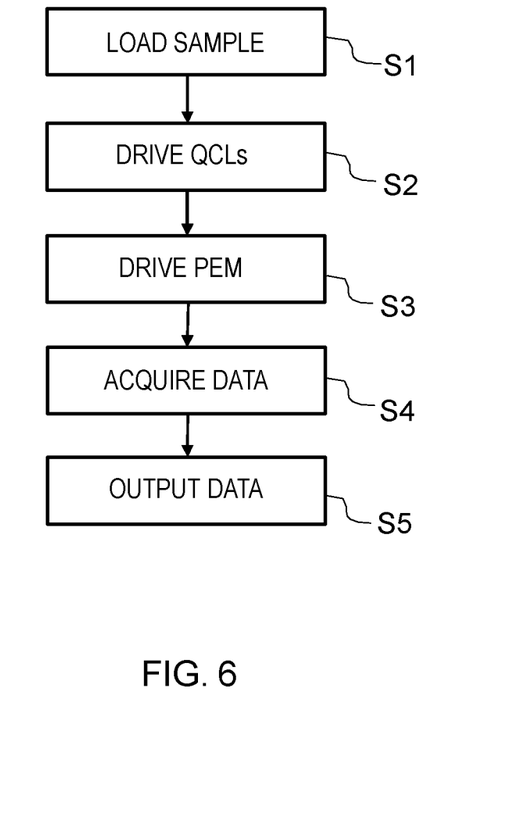
FIG. 6 is a flow diagram showing a method for obtaining a VCD spectrum with a spectrometer according to embodiments of the disclosure.

FIG. 6 is a flow diagram showing a method for obtaining a VCD spectrum with a spectrometer according to any of the above embodiments. In Step S1, a sample is arranged in the sampling beam path of the spectrometer. In Step S2, the two QCLs are driven by the controller via suitable drivers to generate the first and second frequency combs. In Step S3, the PEM is driven to set it in operation at its resonance frequency, so that it will alternately output left and right circularly polarized light from its linearly polarized input light. It will be appreciated that Steps S1 to S3 can be performed in any order. In Step S4, data is acquired at the sample detector (and optional normalizing detector) to measure a differential absorption spectrum from the sample. In Step S5, the acquired VCD data is output from the spectrometer, e.g. to an external computer system for further processing and analysis.

The above described ways for locking the frequency comb beat frequencies are a potential implementation for synchronizing the beat frequencies with the polarization modulation frequency of the polarization modulator. A particular example implementation can be carried out by setting the RF generators that control the FSRs of the frequency combs to be offset with respect to each other by an integer multiple of the polarization modulation frequency. This will ensure that the beat frequencies of the frequency comb C3 are spaced by an integer multiple of the modulation frequency. Using the master-slave configuration to control the relative offset frequency between the frequency combs C1 and C2, the beat frequencies of the frequency comb C3 could be set so each of them is an integer multiple of the polarization modulation frequency, e.g. 2, 3, 4, 5, etc., or 52, 53, 54, 55 etc. or any higher harmonics, e.g. 25, 28, 31, 34, etc. (i.e. increments of more than one).

Figure 7:
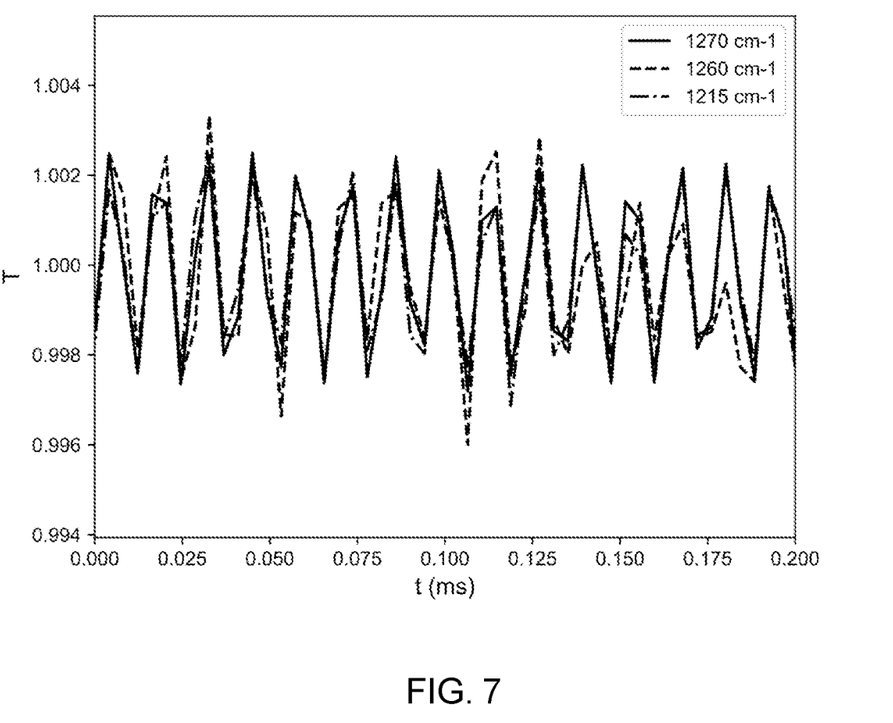
FIG. 7 is a graph of transmission T as a function of time t in milliseconds measured simultaneously at several wavelengths of interest.
Figure 8:
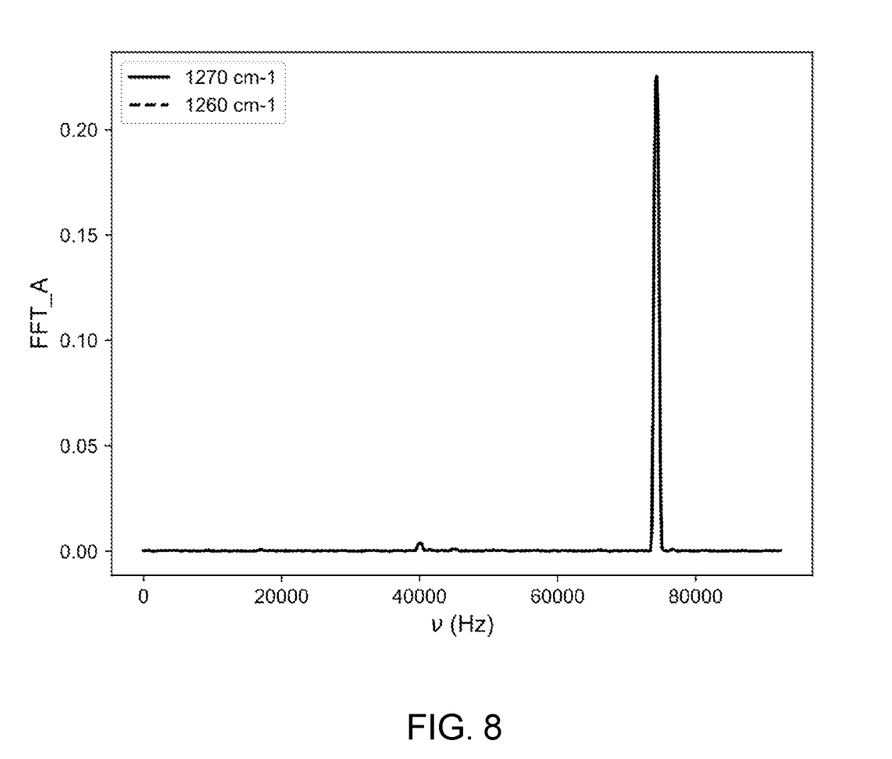
FIG. 8 is a graph of the Fourier-transform of the time-dependent transmission showing high frequency components at first and second harmonics of the polarization modulation frequency.

FIGS. 7 and 8 are graphs referred to in the following description of how a VCD spectrum was obtained in practice. FIG. 7 is a graph of transmission T as a function of time t in milliseconds measured simultaneously at several wavelengths of interest. FIG. 8 is a graph of the Fourier-transform of the time-dependent transmission showing high frequency components at first and second harmonics of the polarization modulation frequency.

A time-resolved infrared spectrum is retrieved from the multi-heterodyne interferogram. The resulting dataset consists of a 2D matrix, containing a microsecond time-resolved time trace of transmission values for each wavelength emitted by the QCL combs. Manipulations such as (weighted) averaging over multiple wavelengths or averaging over multiple acquisitions are performed on the transmission measurements. The periodic modulation of the polarization leads to a periodic modulation of the transmission, which is directly observed in the time resolved transmission measurements shown in FIG. 7. The VCD component of the signals is then obtained by frequency decomposing the transmission time-traces, e.g. by Fourier transform, as shown in FIG. 8. The transmission component at the PEM modulation frequency (here 37 kHz) is termed the VCD signal. As a result of the high time-resolution of the spectral measurements, it will also be possible in many cases to study higher harmonics of the modulation induced signal, as for example visible at 74 kHz in FIG. 8.

The heterodyne beat signals that encode the various wavelengths are at frequencies of 10-1000 MHz. All emission frequencies are evaluated in parallel on a time scale of about 1 microsecond so that a complete frequency/wavelength spectrum is measured every microsecond. The modulation of the polarization (here: 37 kHz corresponding to 27 µs) is therefore much slower than the time needed to retrieve a full transmission spectrum. A complete VCD spectrum is thus obtained on every oscillation of the PEM. Our proposed data acquisition method thus switches the order in which spectral and polarization dependent information are acquired compared to existing VCD implementations. For example, in conventional VCD, the polarization is modulated at a frequency of 10-100 kHz. The tunable QCL source, or a Michelson interferometer, operates at only 10-50 Hz, i.e. three orders of magnitude slower than the polarization modulation. A grating-based system is even slower.

Figure 9:
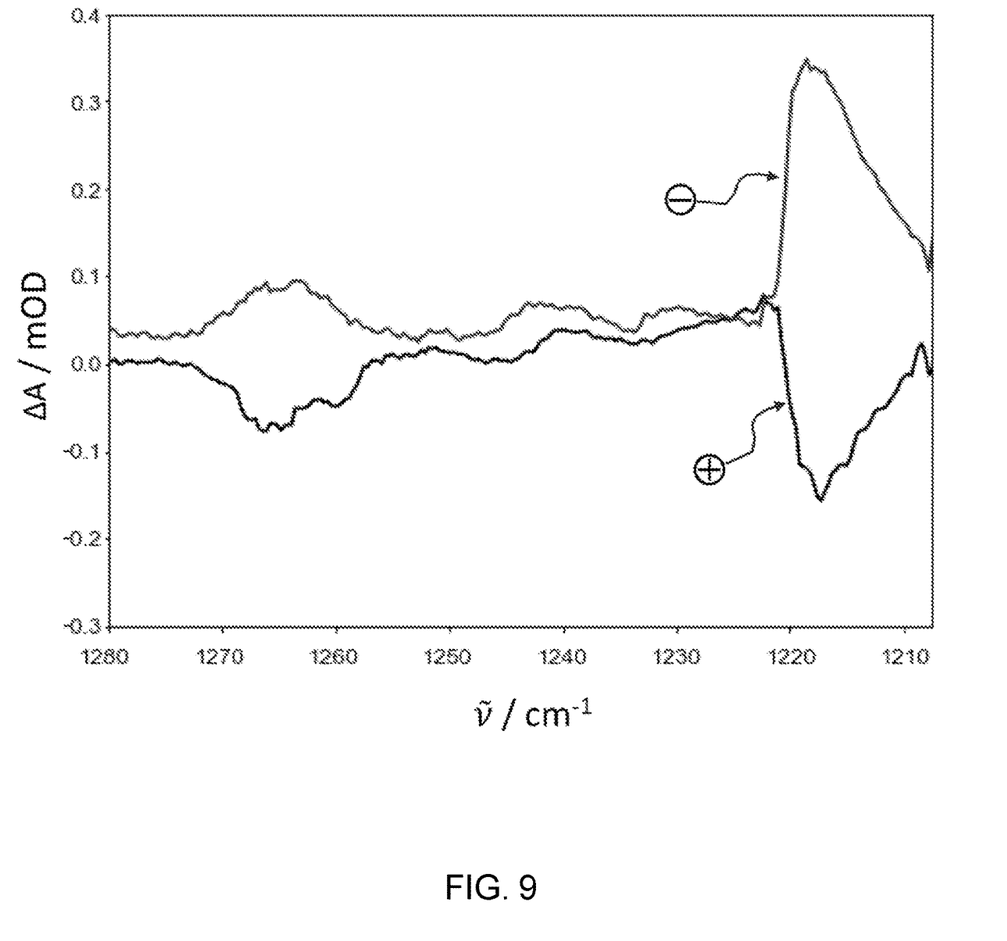
FIG. 9 is a graph of VCD measurement results obtained with a spectrometer according to FIG. 1.

FIG. 9 is a graph of VCD measurement results obtained with a spectrometer according to FIG. 1. The graph shows wavenumber in cm−1 against absorption difference ΔA in units of mOD. The two traces are for samples of (+)-alpha-pinene and (−)-alpha-pinene. The sample cell was a single path transmission cell consisting of two infrared transparent windows separated by a spacer of a given thickness. The graph shows the measured VCD spectrum of a 100 µm thick layer of (+)- and (−)-alpha-pinene. Each of the two traces consists of an average of 100 acquisitions of 16 ms acquisition lengths. That means, a total of only 1.6 seconds of measurement time was used to measure each of the illustrated VCD spectra.

It will be clear to one skilled in the art that many improvements and modifications can be made to the foregoing exemplary embodiment without departing from the scope of the present disclosure.

REFERENCE NUMERALS 5 spectrometer
10 first laser source (local oscillator)
12 second laser source (interrogator)
14 laser driver controller
15 data acquisition module
16 first laser source driver
17 RF-generator for first laser
18 second laser source driver
19 RF-generator for second laser
20 beam splitters
22 mirrors
30 sample photodetector
32 normalizing photodetector
34 amplifiers (A)
36 low-pass filters (LPFs)
38 data acquisition (DAQ) with analogue-to-digital converters (ADCs)
40 computer for control, data logging and data processing
41 storage (memory, hard drive etc.)
42 processor (CPU, GPU, FPGA etc.)
43 frequency demodulator
44 PID controller
46 linear polarizer
48 lens
50 photoelastic modulator (PEM)
52 iris/aperture
54 sample (cell) holder
56 lens S sample (cell)
C1 first frequency comb (local oscillator)
C2 second frequency comb (interrogator)
C3 third frequency comb (mixed first and second at detector)

REFERENCES

1. Keidering, T. A. Instrumentation for Vibrational Circular Dichroism Spectroscopy: Method Comparison and Newer Developments. Molecules 2018, 23, 2404
2. Keidering, T. A. Vibrational Circular Dichroism. Appl. Spectrosc. Rev. 1981, 17, 189-226.
3. Long, F.; Freedman, T. B.; Hapanowicz, R.; Nafie, L. A. Comparison of step-scan and rapid-scan approaches to the measurement of mid-infrared Fourier transform vibrational circular dichroism. Appl. Spectrosc. 1997, 51, 504-507.
4. Rüther, A.; Pfeifer, M.; Lórenz-Fonfría, V. A.; Lüdeke, S. pH Titration Monitored by Quantum Cascade Laser-Based Vibrational Circular Dichroism. J. Phys. Chem. B 2014, 118, 3941-3949.
5. WO 2015/193282 A1

What is claimed is:

1. A method of acquiring a circular dichroism spectrum measuring differential absorption of left and right circularly polarized light by a sample over a wavelength range of interest, the method comprising:
   arranging a sample in a sampling beam path;
   arranging a polarization modulator in the sampling beam path before the sample, the polarization modulator being periodically switchable between two states to output left and right circularly polarized light respectively at a polarization modulation frequency of between 20 kHz to 100 kHz;
   combining first and second light signals containing respective first and second frequency combs into the sampling beam path, the first and second frequency combs consisting of respective finite series of discrete frequencies separated by first and second spacings defined as first and second free spectral ranges respectively;
   arranging a sample detector operable to output a measurement signal in the sampling beam path after the sample, the sample detector having a detection bandwidth that covers a frequency range corresponding to beat frequencies of a third frequency comb that is detected by the sample detector as the measurement signal as a result of heterodyne mixing of the first and second light signals;
   periodically switching the polarization modulator between its two states at a polarization modulation frequency of between 20 kHz to 100 kHz to output left and right circularly polarized light respectively; and
   setting the frequencies of the first and second light signals such that the beat frequencies of the third frequency comb are higher than the polarization modulation frequency by between one and five orders of magnitude so that for each of the left and right circularly polarized light the sample detector's measurement signal measures transmission through the sample across the wavelength range of interest during each period of the polarization modulation.

2. The method of claim 1, wherein the third frequency comb's beat frequencies are synchronized with the periodic switching of the polarization modulator such that each of the beat frequencies is an integer multiple of the polarization modulation frequency.

3. The method of claim 1, wherein the third frequency comb's beat frequencies are between two and four orders of magnitude higher than the polarization modulation frequency.

4. The method of claim 1, the first light signal being output from a first semiconductor laser source serving as a local oscillator, and the second light signal being output from a second semiconductor laser source serving as an interrogator.

5. The method of claim 1, wherein the first and second semiconductor laser sources are quantum cascade lasers.

6. The method of claim 1, wherein the first and second semiconductor laser sources are interband cascade lasers.

7. The method of claim 1, wherein the polarization modulator comprises a linear polarizer arranged in series in the sampling beam path with a photo-elastic modulator, the photo-elastic modulator having a resonance frequency that defines the polarization modulation frequency.

8. The method of claim 1, further comprising:
   using a data acquisition module to collect data from the measurement signal, wherein the data contained in the measurement signal in each period of the polarization modulation is sufficient to determine a differential absorption spectrum over the wavelength range of interest; and
   determining the differential absorption spectrum from the collected data.

9. A circular dichroism spectrometer operable to measure a sample's differential absorption of left and right circularly polarized light over a wavelength range of interest, the spectrometer comprising:
   a polarization modulator that is periodically switchable between two states at a polarization modulation frequency of between 20 kHz to 100 kHz to output left and right circularly polarized light respectively;
   a sample holder configured to receive a sample to be measured in a sample space so that a sample held in the sample holder receives light output from the polarization modulator;
   a first semiconductor laser source, serving as a local oscillator, operable to output a first light signal containing a first frequency comb consisting of a finite series of discrete frequencies separated by a first spacing defined as a first free spectral range;
   a second semiconductor laser source, serving as an interrogator, operable to output a second light signal containing a second frequency comb consisting of a finite series of discrete frequencies separated by a second spacing defined as a second free spectral range;
   a beam combiner configured to receive and superimpose the first and second light signals to form a combined light signal and to direct the combined light signal to be input into the polarization modulator;
   a sample detector operable to output a measurement signal and arranged to receive the combined light signal after it has traversed the sample space, the sample detector having a detection bandwidth that covers a frequency range corresponding to beat frequencies of a third frequency comb that is detected by the sample detector as the measurement signal as a result of heterodyne mixing of the first and second light signals;
   a controller configured to periodically switch the polarization modulator between its two states at a polarization modulation frequency of between 20 kHz to 100 kHz to output left and right circularly polarized light respectively and to output first and second control signals to the first and second semiconductor laser sources to set the frequencies of the first and second light signals such that the resultant beat frequencies of the third frequency comb are higher than the polarization modulation frequency by between one and five orders of magnitude so that for each of the left and right circularly polarized light the sample detector's measurement signal measures transmission through the sample across the wavelength range of interest during each period of the polarization modulation; and a data acquisition module arranged to collect data from the measurement signal and configured to determine a differential absorption spectrum for a sample over the wavelength range of interest from the collected data.

10. The spectrometer of claim 9, wherein the controller is further configured to synchronize the third frequency comb's beat frequencies with the periodic switching of the polarization modulator.

11. The spectrometer of claim 10, wherein each of the third frequency comb's beat frequencies is set to be an integer multiple of the polarization modulation frequency.

12. The spectrometer of claim 9, wherein the controller sets the first and second frequencies of the first and second light signals such that third frequency comb's beat frequencies are between two and four orders of magnitude higher than the polarization modulation frequency.

13. The spectrometer of claim 9, wherein the first and second semiconductor laser sources are quantum cascade lasers.

14. The spectrometer of claim 9, wherein the first and second semiconductor laser sources are interband cascade lasers.

15. The spectrometer of claim 9, wherein the polarization modulator comprises a linear polarizer and a photo-elastic modulator arranged in series, the photo-elastic modulator having a resonance frequency that defines the polarization modulation frequency.

16. The spectrometer of claim 9, further comprising a frequency demodulator arranged to extract an error signal from the measurement signal, the error signal being fed back to the controller, the controller being configured to determine a correction signal from the error signal in a control loop to at least one of the first and second semiconductor laser sources derived from the error signal so as to lock the first semiconductor laser source to the second semiconductor laser source in a master-slave configuration.

17. The spectrometer of claim 9, further comprising a first RF generator operable to generate a first reference signal at a first RF frequency that is matched to the first free spectral range, the first RF generator being connected to inject the first reference signal into the cavity of the first semiconductor laser source to lock the first free spectral range to the first RF frequency.

18. The spectrometer of claim 17, further comprising a second RF generator operable to generate a second reference signal at a second RF frequency that is matched to the second free spectral range, the second RF generator being connected to inject the second reference signal into the cavity of the second semiconductor laser source to lock the second free spectral range to the second RF frequency.

* * * * *